(12) United States Patent
Pernot et al.

(10) Patent No.: US 9,597,092 B2
(45) Date of Patent: Mar. 21, 2017

(54) MECHANIZED SURGICAL EQUIPMENT COMPRISING AN INSTRUMENT AND AN INSTRUMENT HOLDER, CORRESPONDING PACKAGING AND INSTRUMENT HOLDER

(75) Inventors: Jacques Pernot, Vieilley (FR); Hubert Euvrard, Besancon (FR); Emilien Paul, Ranchot (FR)

(73) Assignee: NEOLIX, Chatres-la-Foret (FR)

( * ) Notice: Subject to any disclaimer, the term of this patent is extended or adjusted under 35 U.S.C. 154(b) by 674 days.

(21) Appl. No.: 14/006,895

(22) PCT Filed: Mar. 21, 2012

(86) PCT No.: PCT/EP2012/055028
§ 371 (c)(1),
(2), (4) Date: Jan. 30, 2014

(87) PCT Pub. No.: WO2012/126957
PCT Pub. Date: Sep. 27, 2012

(65) Prior Publication Data
US 2014/0163555 A1    Jun. 12, 2014

(30) Foreign Application Priority Data
Mar. 21, 2011    (FR) ...................... 11 52287

(51) Int. Cl.
*A61B 17/16*    (2006.01)
*A61C 1/14*    (2006.01)
(Continued)

(52) U.S. Cl.
CPC ............ *A61B 17/162* (2013.01); *A61B 50/22* (2016.02); *A61B 50/30* (2016.02); *A61C 1/14* (2013.01);
(Continued)

(58) Field of Classification Search
CPC ... A61B 17/162; A61B 50/3001; A61C 1/144; A61C 1/14; A61C 1/082; A61C 1/16
See application file for complete search history.

(56) References Cited

U.S. PATENT DOCUMENTS 3,794,091 A * 2/1974 Ersek ...................... A61B 1/07
150/154
4,859,182 A * 8/1989 Nerli ........................ A61C 1/16
128/919

(Continued)

FOREIGN PATENT DOCUMENTS

DE         2746313 A1    4/1979
DE    10146905 A1 *    7/2003
(Continued)

OTHER PUBLICATIONS

French Search report and Written Opinion dated Nov. 15, 2011 for corresponding French Application No. 1152287, filed Mar. 21, 2011.
(Continued)

*Primary Examiner* — David Bates
(74) *Attorney, Agent, or Firm* — David D. Brush; Westman, Champlin & Koehler, P.A.

(57) ABSTRACT

A piece of mechanized surgical equipment is provided, which includes an instrument holder having an element for receiving and retaining a surgical instrument for mechanized use. Also provided is a surgical instrument for mechanized use and configured to be mounted on the instrument holder. The element for receiving and retaining is mobile between an unlocking position, in which the element enables insertion of the instrument into the instrument holder or withdrawal thereof, and a locking position, in which the element prevents the withdrawal of the instrument from the instrument holder. Furthermore, the equipment includes a case in which an active blade of the instrument can be removably housed, the case having an engaging element for engaging
(Continued)

with the receiving and retaining element so as to cause the element to move from the unlocking position to the locking position, or vice versa.

12 Claims, 8 Drawing Sheets

(51) Int. Cl.

| | | |
|---|---|---|
| A61C 3/02 | (2006.01) | |
| A61C 5/02 | (2006.01) | |
| A61C 8/00 | (2006.01) | |
| A61C 3/04 | (2006.01) | |
| A61B 17/00 | (2006.01) | |

(52) U.S. Cl.
CPC .............. *A61C 1/141* (2013.01); *A61C 1/144* (2013.01); *A61C 3/02* (2013.01); *A61C 5/023* (2013.01); *A61C 8/0089* (2013.01); *A61B 50/3001* (2016.02); *A61B 2017/00464* (2013.01); *A61B 2017/00473* (2013.01); *A61C 3/04* (2013.01); *A61C 2202/00* (2013.01)

(56) References Cited

U.S. PATENT DOCUMENTS

| | | | | | |
|---|---|---|---|---|---|
| 5,197,875 | A | * | 3/1993 | Nerli | ................. A61C 17/0202 433/116 |
| 5,593,391 | A | * | 1/1997 | Stanners | ............... A61M 5/322 604/110 |
| 6,058,807 | A | * | 5/2000 | Fujii | ..................... B23B 31/005 408/226 |
| 6,695,321 | B2 | * | 2/2004 | Bedi | ..................... B25B 15/001 279/22 |
| 2006/0110703 | A1 | * | 5/2006 | Bills | ....................... A61C 5/023 433/102 |
| 2011/0171595 | A1 | * | 7/2011 | Turner | ..................... A61C 1/08 433/127 |

FOREIGN PATENT DOCUMENTS

| | | | |
|---|---|---|---|
| DE | 10146905 | A1 | 7/2003 |
| EP | 1836991 | A1 | 9/2007 |
| EP | 2123233 | A1 | 11/2009 |
| FR | 2985658 | * | 7/2013 |
| WO | 88/05289 | A1 | 7/1988 |

OTHER PUBLICATIONS

International Search Report dated May 22, 2012 for corresponding International Application No. PCT/EP2012/055028, filed Mar. 21, 2012, 8 pages.
International Preliminary Report on Patentability and English Translation of the Written Opinion dated Sep. 24, 2013 for corresponding International Application No. PCT/EP2012/055028, filed Mar. 21, 2012, 10 pages.

* cited by examiner

Fig. 15 they grasp it with dental tweezers.

MECHANIZED SURGICAL EQUIPMENT COMPRISING AN INSTRUMENT AND AN INSTRUMENT HOLDER, CORRESPONDING PACKAGING AND INSTRUMENT HOLDER

1) CROSS-REFERENCE TO RELATED APPLICATIONS

This application is a Section 371 National Stage Application of International Application No. PCT/EP2012/055028, filed Mar. 21, 2012 and published as WO 2012/126957 on Sep. 27, 2012, not in English.

2) FIELD OF THE INVENTION

The field of the invention is that of the designing and manufacture of surgical apparatuses. More specifically, the invention pertains to mechanized surgical apparatuses comprising instruments for mechanized use (rotary, vibrating and gyrating instruments, etc). The invention pertains especially to apparatuses comprising surgical instruments such as drills, burs, blades and, in the field of dental surgery (odontology), endodontic instruments, dental burs, implant posts and scaling curettes.

The example dealt with, by way of illustration but non-exhaustively, pertains to dental surgical apparatuses. However, the invention can also be applied to other types of surgical equipment such as for example mechanized equipment which can be used in orthopedic surgery.

3) PRIOR ART

A mechanized surgical tool is a tool enabling the transmission of motion to a surgical instrument which for example can be a rotational motion, a vibrating motion, or a gyrating motion (i.e. a motion in which the instrument rotates alternately in one direction and then in the other).

Mechanized surgical tools generally result from the assembly of two components, namely:
  an instrument constituting the specific tool needed for the surgical act, and
  an instrument-holder such as for example a handpiece or a contra-angle equipped with means for receiving, retaining and possibly actuating the instrument.

Classically, a surgeon or a dentist must use several instruments in succession during an operation on a patient.

This is why the instrument-holder is designed to be compatible with several models of instruments.

The patent application filed under number EP 2123 233 describes an example of an instrument-holder that facilitates the setting up and retaining of a dental surgical instrument. According to the technique described, the instrument-holder is equipped with locking/unlocking means which take the form of an integrated pushbutton, actuated by a finger with which the dentist holds the instrument-holder. Pressure on the pushbutton acts on the instrument-holder in loosening the instrument-retaining means (jaws, clamps, lever, bolt, etc) and therefore releases the instrument. Conversely, releasing the pushbutton applies a force on the retaining means so that they grip an instrument pre-inserted into the instrument-holder.

These locking/unlocking means can take other forms (pull-rod, push-rod) inducing the same mode of retaining the instrument.

In practice, the practitioner grasps an instrument between the thumb and forefinger of one of his hands, possibly gloved, or he grasps it with dental tweezers.

Then, he inserts this instrument into the instrument-holder which he holds in the other hand in pressing the pushbutton (or actuating any other locking/unlocking means) with a finger of this other hand.

Similarly, the practitioner must press the pushbutton with one hand to axially release the instrument and remove it with the other hand.

Thus, the instrument and the instrument-holder make use of both hands of the practitioner and require that the practitioner exert pressure with a finger and, in addition, they require him to maintain this pressure so long as the instrument has not completely come out or has not been completely inserted into the holder.

It can be noted that the requirements of assembly are even greater with certain instruments such as those of the type 1 according to the NF EN ISO 1797 standard, having a diameter of 2.35 mm, a groove and a flat section and are intended for connection to a contra-angle. Indeed, the practitioner in this case must orient the instrument angularly in the instrument-holder while at the same time exerting continuous pressure on the pushbutton in order to make the flat section of the instrument, constituting a male part, coincide with a female part constituted by a hole present in the instrument-holder. Once the appropriate position has been found, the practitioner can release the pushbutton and the instrument is then held locked on the instrument-holder, axially and in rotation. The motion generated by any actuating means integrated into the instrument-holder can then be transmitted to the instrument.

Besides, the instrument-holder and the instrument are supposed to be sterile before being assembled with each other so that the assembled apparatus is itself sterile when it is inserted into the patient's mouth.

Now, the mode of assembly described here above implies firstly direct contact between the fingers of the practitioner's hand and the instrument on the one hand and secondly direct contact between the practitioner's other hand and the instrument-holder, at the pushbutton and the surrounding parts (such as the head of the contra-angle). This therefore causes a major risk of contamination of the assembled equipment.

This drawback is especially great when it is necessary to search for the flat section of the instrument by handling the instrument in the instrument-holder. Indeed, this operating mode gives rise to a particular ergonomical difficulty as well as uncertainty as to the efficient locking of the system. This leads certain practitioners not to wear gloves so as to obtain greater touch sensitivity. The risk of contamination is therefore significantly increased in this case.

Besides, gloves do not provide an absolute guarantee of asepsis because they can themselves get contaminated, perforated, etc. Direct contact between the practitioner's hands and the instrument and the instrument-holder therefore always gives rise to a major health hazard for the patient.

4) SUMMARY OF THE INVENTION

These goals as well as others that shall appear here below are achieved through the invention, the object of which is a mechanized surgical apparatus comprising:
  at least one instrument-holder comprising means for receiving and retaining a surgical instrument for mechanized use, and
  at least one surgical instrument for mechanized use to be mounted on said instrument-holder, said instrument comprising a shank intended for cooperating with the instrument-holder and an active blade.

According to the invention, said means for receiving and retaining are mobile between:

- an unlocking position, in which they enable the introduction of said shank of the instrument into the instrument-holder or the withdrawal of said shank from the instrument-holder; and
- a locking position in which they prevent the withdrawal of said shank from the instrument-holder;

and the mechanized surgical apparatus comprises a case in which said active blade of said instrument can be housed detachably, said case having an cooperating element for cooperating with said means for receiving and retaining to cause them to pass from said unlocking position to the locking position, or vice versa.

In this way, the mounting of the instrument on the instrument-holder or its dismounting can be done without any contact being necessary between the practitioner and the instrument, the active blade of which is housed in the case, and in limiting the contacts needed at the head of the instrument-holder.

The shank of the instrument is placed and can be maintained in position in the instrument-holder without the practitioner having to press on an actuating push-button type unit integrated into the instrument-holder.

The locking or the unlocking of the position of this shank of the instrument in the instrument-holder, enabling respectively the use of the instrument and its dismantling from the instrument-holder, is obtained by a simple action of the case on the receiving and retaining means of the instrument-holder. Indeed, the actuating unit which enables the means for receiving and retaining to pass from the locking position to the unlocking position is situated in proximity to the location intended for receiving the shank of the instrument, in order that it can be actuated by the case in which the active blade of this instrument is housed. In addition, the case itself has a configuration adapted to obtaining an actuation.

The equipment of the invention therefore enables use in ergonomic and aseptic conditions better than those of the prior-art techniques.

Besides, the case can facilitate the visual or computer-based identification of the instrument that it contains, which is small-sized and can sometimes be mistaken for other similar instruments.

Advantageously, said unlocking and locking positions of the means for receiving and retaining are stable positions.

Thus, the practitioner can easily insert the shank of the instrument into the instrument-holder or remove it from the instrument-holder when the means for receiving and retaining are in their stable unlocking position. When the shank of an instrument is inserted into the instrument-holder, the practitioner can act on the case so that its cooperating element acts on the means for receiving and retaining to cause them to pass into the locking position so that the shank of the instrument is firmly retained. This locking position is also stable, and this prevents an accidental unlocking of the shank of the instrument. Further action by the cooperating element of the case on the means for receiving and retaining enables a return to the stable unlocking position. Thus, these means for receiving and retaining which are bistable, i.e. they can be placed in two distinct stable positions, enable very easy use of the mechanized surgical apparatus in compliance with conditions of asepsis.

According to a preferred embodiment, said means for receiving and retaining comprise:

- a receptacle to receive and maintain said shank of the instrument, said receptacle being mobile between an open position, permitting the introduction of said shank into said receptacle or the withdrawal of said shank from said receptacle, and a retaining position in which it retains said shank in said receptacle;
- a locking/unlocking unit, mobile between said locking position in which it holds said receptacle in said retaining position, and said unlocking position in which it does not hold said receptacle in said retaining position;

and said cooperating element of said case is shaped to cooperate with said locking/unlocking unit to cause it to pass from said locking position to said unlocking position, or vice versa.

Thus, by a simple action on the locking/unlocking unit, this unit can alternate between a locking position, in which the instrument is firmly retained in the receptacle and an unlocking position in which the mobility of the receptacle enables the mounting and dismounting of the shank of an instrument.

Furthermore, when the locking/unlocking unit is in its unlocking position, the receptacle can be in a retaining position enabling an instrument to be held in the instrument-holder but in an unlocked way so that a manually applied force is sufficient to extract the instrument from the instrument-holder in making the receiving element pass from its retaining position to its open position.

It must be noted that, preferably, the receptacle is stable in its retaining position and unstable in its open position. Thus, it remains in its retaining position by default so long as a force generated by the introduction of the shank of an instrument or the withdrawal of this shank does not lead it into the open position.

The retaining force of the instrument can therefore be staged according to the position (locking/unlocking) of the locking/unlocking unit between a firm hold which enables the use of the instrument and a weak hold which enables the withdrawal of the instrument. This staging helps improve the ergonomy of use of the equipment because it prevents the instrument from falling from the instrument-holder when the means for receiving and retaining are in unlocking position. It thus facilitates the mounting and dismounting of the instrument.

The receptacle can have an internal shape that is complementary to the external shape of a large number of instruments, enabling it to be compatible and efficient especially with the large number of instruments having a flat section.

During the maintenance operations or operations for changing the type of instrument installed, the receptacle can be easily replaced without requiring any replacement of other instrument-holder components. The external shape of the receptacle can, for this purpose, be designed according to a standard, enabling the locking/unlocking unit to be compatible with the different models of receptacles.

According to one advantageous approach, said instrument-holder comprises a body in which the locking/unlocking unit can be mounted slidingly, said locking/unlocking unit having at least one mobile catch intended to cooperate with at least one housing made in said body.

Action by the case can thus easily activate the sliding of the locking/unlocking unit in order to prompt the locking/unlocking unit to pass between its locking and/or unlocking positions.

The practitioner then only needs to make the case exert pressure on the locking/unlocking unit to enable the receptacle to freely pass from its open position, enabling an instrument to be brought out or inserted, or on the contrary to enable this receptacle to firmly hold this instrument.

The cooperating of a catch with a housing also makes it possible to keep one or more positions of the locking/unlocking unit stable in the body. Thus, this position of the locking/unlocking unit is kept even if the practitioner relaxes pressure on the case. This is constitutes an advantage when the practitioner has to introduce and position the instrument rotationally in the instrument-holder.

The alternation between several stable positions of the locking/unlocking unit in the body is done through the mobility of the catch, activated by the sliding motion of the locking/unlocking unit.

Advantageously, said catch is radially and laterally mobile.

The mobility of the catch, which is both radial and lateral, indeed makes it possible, with an adapted shape of the catch and the housing, to dictate the order of the positions that the locking/unlocking unit can occupy successively in the body, for example so as to bypass certain stop positions. Thus, the mounting and dismounting of the instrument can be done by actuating the locking/unlocking unit by means of the case, in always following the same sliding direction.

For example, the sliding achieved by pressure of the case on the locking/unlocking unit can enable passage from a first position, a stable position in which the instrument is retained and locked in the instrument-holder, to a second position, a stable position in which the instrument is held in an unlocked way in the instrument-holder: by prolonging this sliding motion, always in the same sense, it is possible to reach a non-stable position in which the instrument is always retained in an unlocked way, making it possible to return to the first position by means of return means without the catch being able to stop in the second position.

In other words, the catch is mobile along directions that enable it to follow a different path when passing from the locking position to the unlocking position and when passing from the unlocking position to the locking position, making it possible to obtain these two passages in keeping the same sense of sliding and therefore in exerting the same actuation of the locking/unlocking unit.

Thus, the practitioner can mount and dismount his instrument-holder instruments by a simple and intuitive action. Since the actuating interface is constituted solely by a case, the action of which is concentrated on the locking/unlocking unit, the improvement in ergonomy is accompanied by an improvement in the aseptic conditions of use of the equipment.

It can be noted that the body referred to, included in the instrument-holder and in which the housing is made, can be:
  fixed relative to the frame of the instrument-holder (it can then form part of this frame);
  mobile relative to the frame of the instrument-holder, especially when it takes part in driving the motion of the instrument (rotationally in particular).

Preferably, said catch is elastically deformable.

Thus, it can brought without force or excessive friction into several positions relative to the body of the instrument-holder and especially a position in which it penetrates the housing with a force which provides for the stability of the position of the locking/unlocking unit relative to the body and, at the same time, can be easily overcome when the practitioner, using the case, wishes to cause the locking/unlocking unit to slide.

Such a catch can comprise one or more mechanical elements with a spring system. However, it will preferably be made out of a flexible, plastic or metallic material, similarly to the entire locking/unlocking unit.

Advantageously, said locking/unlocking unit is mounted slidingly relative to said receptacle.

This sliding motion can then be used to bring the locking/unlocking unit in a first stage into the unlocking position, in which the receptacle can pass from its retaining position to its open position permitting the introduction of the instrument into the instrument-holder or the withdrawal of the instrument from the instrument-holder and then, in a second stage, into the locking position in which it keeps the receptacle in its position of retaining the instrument in the instrument-holder.

The locking/unlocking unit can be mounted slidingly both relative to the body of the instrument-holder and relative to the receptacle, which can advantageously be fixed relative to the body of the instrument-holder.

The sliding motion is then unique and common. It concerns only the locking/unlocking unit, and the joining of this device with the body and the receptacle can be designed to be all the more compact, solid and efficient in retaining the instrument.

In order to convert this sliding motion into a holding of the receptacle in its position of retaining the instrument, complementary shapes (conical shapes for example) can be adapted on the receptacle and on the locking/unlocking unit.

According to a preferred solution, said receptacle has a base provided with at least one radially mobile toe, said shank of the instrument having at least one recess to receive said toe in said retaining position.

In this way, in the retaining position of the receptacle, the instrument is retained axially in the receptacle through the application of a radial force on at least one toe, which may take the form of a tip, a ridge or any other set of tips, whether continuous or discontinuous, the radial force enabling this toe to take position in a recess of the instrument, such as a groove, to prevent its withdrawal or, at least, to ensure that a minimum manual force is exerted to withdraw it.

Each toe of a receptacle can occupy a position, in the open position of the receptacle, that is at a greater distance radially than when it retains an instrument, when the receptacle is in a retaining position. This open position enabling the introduction and withdrawal of an instrument is advantageously an unstable position.

The radially mobile toe is held in a locked manner in the position enabling the instrument to be retained through the above-mentioned sliding of the locking/unlocking unit into its locking position, in which it exerts a gripping by the receptacle on the instrument preventing the movement of the toes into the open position.

Thus, an instrument to be introduced into an instrument-holder can be:
  oriented rotationally in the receptacle through the presence of one or more flat surfaces or flat sections on the shank of the instrument cooperating with the interior of the receptacle;
  retained axially in the receptacle through the presence of one or more toes, which are radially mobile at the base of the receptacle and cooperate at the recesses in the instrument;
  retained in a locked manner within the receptacle by contact between the toes and a recess of the shank of the instrument, even by contact of the interior of the receptacle with the flat surfaces or flat sections of the shank of the instrument.

It can be noted that the elasticity of the receptacle can make it possible to eliminate the clearance between the instrument-holder and the instrument, thereby improving their cooperating (reducing vibrations as well as improving the tactile feeling (finer sensations) on the part of the practitioner.

Advantageously, the instrument-holder comprises a return spring between said body and said locking/unlocking unit, said spring tending to push said locking/unlocking unit towards said locking position.

During the mounting of the locking/unlocking unit slidingly in the body, this spring can thus be installed in a compressed position between these two elements in such a way that it exerts a continual thrust on the locking/unlocking unit towards a locking position.

Pressure by the case on the locking/unlocking unit in the sense contrary to the pressure exerted by the spring on the locking/unlocking unit then enables this unit to slide up to an unlocking position in which the receptacle can pass into its open position to permit the introduction of the instrument into the instrument-holder or the withdrawal of the instrument from the instrument-holder.

The spring contributes to stabilizing the locking/unlocking positions of the locking/unlocking unit, possibly as a complement to the cooperating of the catch with a housing in the body in eliminating clearances that could be present in these positions.

Thus, the practitioner not only benefits from being able to relax the pressure exerted by the case on the locking/unlocking unit but also gains in precision and in touch sensitivity when he introduces the instrument into the instrument-holder.

Then, a new compression and then a relaxing of the spring enable the locking/unlocking unit to leave its unlocking position and take the locking position in which it maintains the locking unit in the instrument-retaining position.

The spring therefore constitutes a return means that is simple to implement with the sliding of the locking/unlocking unit in the body and contributes to bringing it into different stable positions in which the practitioner can easily use the instrument or mount or dismount it.

The ergonomy of use and therefore the conditions of asepsis are improved because the practitioner needs to neither touch the instrument (he acts on the case in holding the instrument-holder) nor exert continued pressure on the locking/unlocking unit to install the instrument.

When the instrument is being introduced, the solidity of the firmness with which the instrument is held on the instrument-holder is verified naturally, without any additional gestures on the part of the practitioner, owing to the very fact that the instrument remains retained on the instrument-holder and no longer gripped in the case clamped by the practitioner.

Advantageously, said locking/unlocking unit has a part extending out of the body of the instrument-holder.

In this way, the locking/unlocking unit remains visible and easily accessible to the practitioner who must act on this locking/unlocking unit by means of the case when he wishes to install or dismount an instrument.

This also means that the locking/unlocking unit which is mobile relative to the body of the instrument-holder does not completely enter the volume of the body without external action, such as pressure of the case. The return spring, especially, can then especially contribute to allowing the locking/unlocking unit to present a part extending by default out of the body of the instrument-holder.

Preferably, said part is cylindrical.

This shape is favorable to a homogenous distribution of the stresses transmitted by means of the case with which the part is likely to cooperate when the practitioner wishes to install or dismount an instrument, especially when the cooperating element of the case is a ring.

Besides, this cylindrical shape can make it possible to fill the clearances and recesses present between the body of the instrument-holder and the receptacle and thus limit risks of clogging or even jamming when the locking/unlocking unit is in motion.

Preferably, said cooperating element of the case is a ring. Thus, the force exerted on the case can be uniformly distributed on the surface of a ring-shaped part centered on the instrument during the mounting and dismounting operations which bring the case to cooperate with the locking/unlocking unit.

An object of the invention is also an assembly constituted firstly by a surgical instrument for mechanized use comprising a shank that is to cooperate with the receiving and retaining means of an instrument-holder and an active blade and secondly by a case, said active blade being housed detachably in said case, wherein said case has a cooperating element shaped to cooperate with said means for receiving and retaining to cause them to pass from an unlocking position, in which they enable the introduction of said shank of the instrument into the instrument-holder or the withdrawal of said shank from the instrument-holder, into a locking position in which they prevent the withdrawal of said shank from the instrument-holder, or vice versa.

The instrument also pertains to an instrument-holder comprising means for receiving and retaining a shank of a surgical instrument for mechanized use in which said means for receiving and retaining are shaped to cooperate with a cooperating element linked to said surgical instrument to cause said receiving and retaining means to pass from an unlocking position, in which they enable the withdrawal of said shank from the instrument-holder, to a locking position in which they prevent the withdrawal of said shank from the instrument-holder, or vice versa.

5) LIST OF FIGURES

Other features and advantages of the invention shall appear more clearly from the following description of embodiments of the invention given by way of illustratory and non-exhaustive examples, and from the appended drawings, of which.

6) DESCRIPTION OF PREFERRED EMBODIMENTS OF THE INVENTION

6.1. Mechanized Surgical Equipment

As indicated here above, the principle of the invention lies in the fact of making a mechanized surgical apparatus comprising an instrument-holder and an instrument that is to be assembled and disassembled without the practitioner having to touch either the instrument or the head element of the instrument-holder.

The embodiments which are described here below, with reference to the figures, pertain to a mechanized surgical equipment of this kind intended for dental surgery. The invention, however, is not limited to these possible applications to the field of dental surgery. Those skilled in the art can thus without any difficulty implement it in other fields of surgery implementing surgical equipment with mechanized use, as for example in the field of orthopedic surgery in which instruments for mechanized use, such as drills for example, are commonly used.

Figure 1:
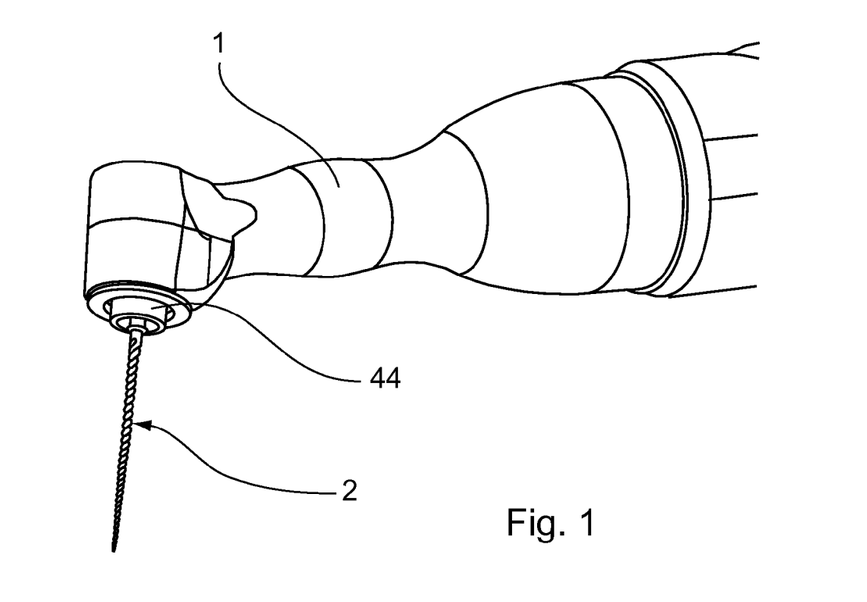
FIG. 1 is a partial illustration, in a perspective view, of an assembly formed by an instrument-holder and a dental surgical instrument according to one embodiment of the invention.

Referring to FIG. 1, an apparatus for dentists comprises two components fixedly attached to each other during a surgical operation:
an instrument-holder 1, in this case an contra-angle head forming an instrument-holding unit, and
a surgical instrument 2, or drill, forming the active part of the equipment, mounted in the instrument-holder.

6.2. Surgical Instrument

Figure 2:
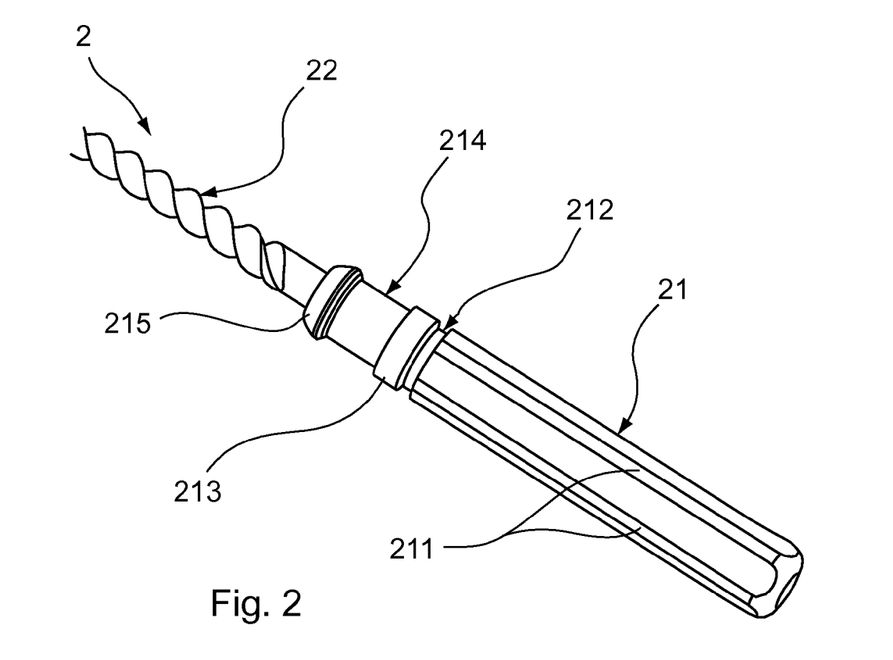
FIG. 2 is a partial illustration, in a perspective view, of an instrument according to one embodiment of the invention.

In FIG. 2, the instrument 2 which is of a generally cylindrical shape comprises a shank 21 that is to cooperate with the instrument-holder and an active blade 22 that is to enter the mouth of the patient being operated on by the dentist. The instrument must therefore remain sterile, especially at the level of the active blade 22.

Figure 3A:
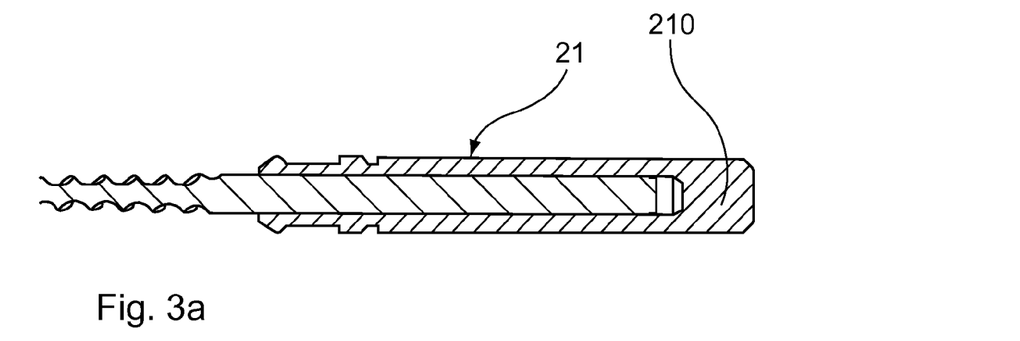
FIGS. 3a, 3b and 3c are partial illustrations, in section, of an instrument in three preferred embodiments of the invention.
Figure 3B:
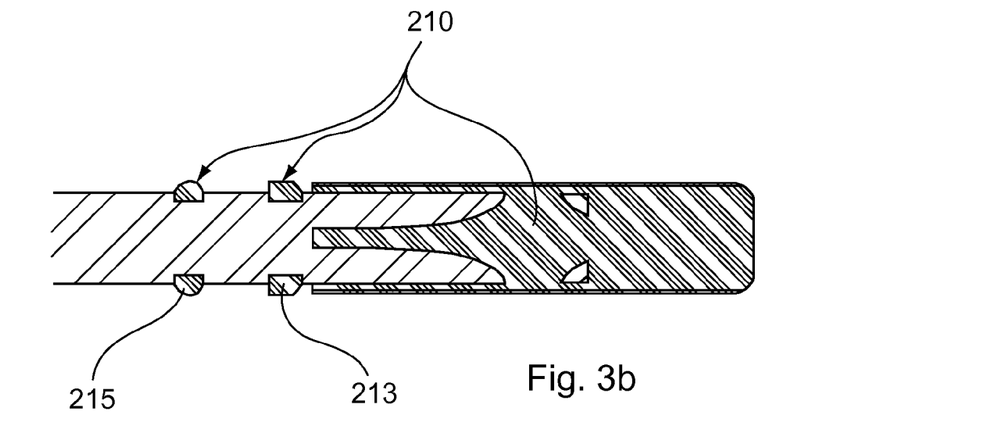
Figure 3C:
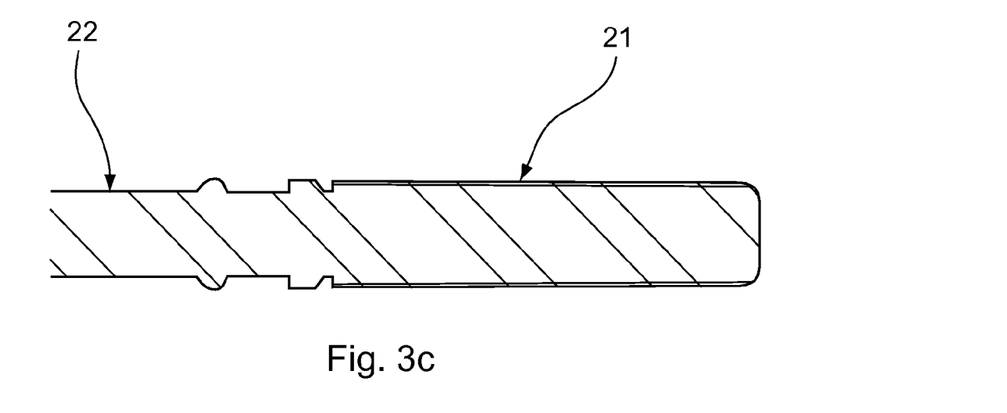
Figure 4:
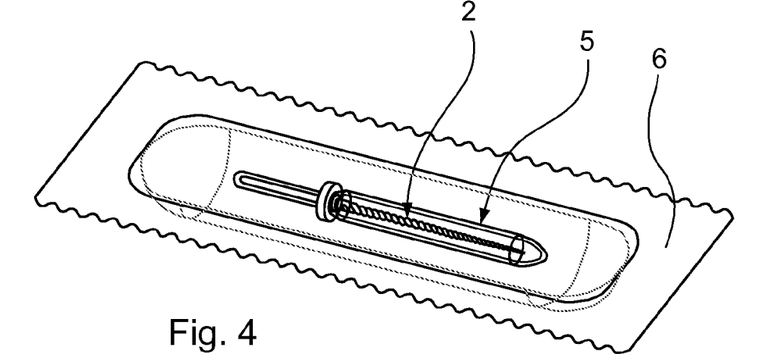
FIG. 4 is an illustration, in a front view, of an instrument, a case and a means of packaging according to one embodiment of the invention.

The instrument 2 is preferably made by plastic overmolding (as illustrated in FIGS. 3a and 3b) or as one piece (FIG. 3c).

The instrument 2 can also be made with a metal or plastic shank 21, mounted so as to be tightly fitted to the blade 22.

The overmolding is done in one piece 210 (FIG. 3a) in which case it then constitutes the shank 21, or it can be made in several parts 210 (FIG. 3b).

The active blade 22 is always made of a metallic material.

In the case illustrated in FIG. 2, the shank 21 comprises flat surfaces 211 intended to hold the instrument 2 rotationally.

In its part closest to the active blade 22, the shank 21 also has two grooves 212, 214 separated by a stop ring 213 including a shoulder. A beveled ring 215 (which could also have a substantially rounded shape, as on an embossment) marks the junction between the groove 214 and the active blade 22.

It can be noted in the example illustrated in FIG. 3b that the stop ring 213 and beveled ring 215 constitute parts 210 that are overmolded in a dissociated way.

6.3. Assembly Formed by the Instrument and the Case

FIGS. 4 to 7 present an assembly constituted by the instrument 2 and a case 5 while the active blade 22 is housed in a case 5. This case is an integral part of the packaging of the instrument. It enables the transportation and handling of the instrument without touching its active blade 22.

Figure 5A:
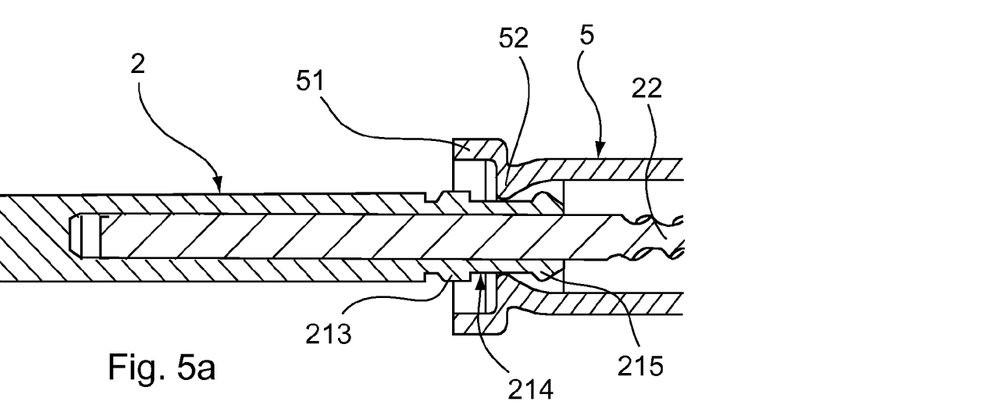
FIGS. 5a and 5b are partial illustrations, in section, of the assembling of an instrument in a case made according to two preferred embodiments of the invention.
Figure 5B:
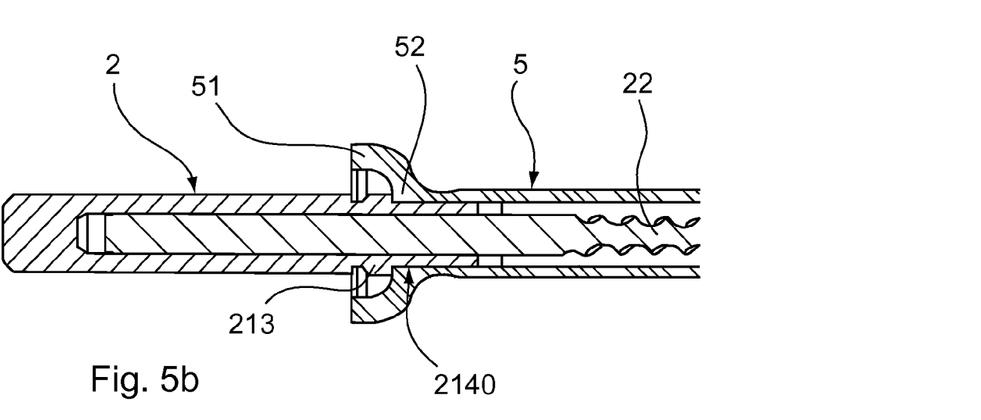

FIGS. 5a and 5b illustrate two preferred embodiments of an assembly constituted by an instrument and a case 5.

FIG. 5a illustrates an instrument 2 that is overmolded or has an added-on metal or plastic shank (such as in FIG. 3a), the active blade of which is in a semi-rigid case 5 made for example out of a plastic material. The case has at least one flexible inner lip 52 designed to slide along the groove 214 of the instrument. The stop ring 213 constitutes an abutment, designed especially to prevent the instrument from falling into the bottom of the case (which would risk damaging the active blade 22) while the beveled ring 215 is an obstacle to the sliding motion, which can be overcome by simple manual force, to withdraw the instrument from the case or introduce it therein.

In the example illustrated, the inner lip is unique, with a ring shape and it cooperates with the groove 214 at the level of a diameter of this groove.

FIG. 5b illustrates another instrument 2 which is different by the fact that it does not have the beveled ring as in the previous example. This instrument 2 is in another flexible case 5, made out of a material such as silicone. The case has another elongated inner lip 52 in the form of a cylindrical sheath intended to slide along a smooth cylindrical end 2140 of the instrument. The case is represented in a positioning abutting the stop ring 213 of the instrument. In this case, it is friction between the inner lip and the smooth cylindrical end 2140 that constitutes an obstacle to the sliding which can be overcome by a simple manual force to extract the instrument from the case or introduce it therein.

It can be noted that, in any case, the ring 51 of the case has sufficient rigidity to withstand a manual force with a longitudinal thrust.

Figure 6:
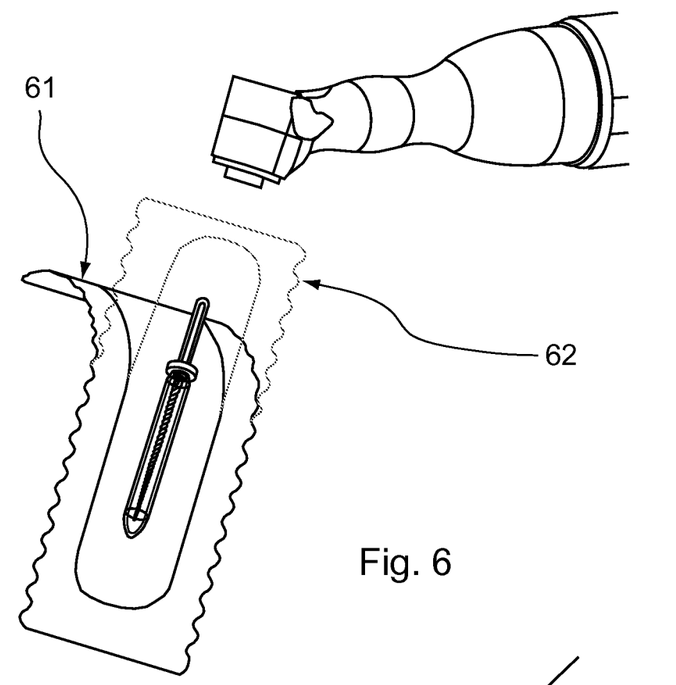
FIG. 6 is an illustration, in perspective, of the instrument-holder of FIG. 1 (seen partially) and the instrument, the case and the means for packaging of FIG. 4, the partially open means of packaging containing the case and, inside the case, the instrument.

In order to further improve the conditions of asepsis in which the apparatus can be used by the dentist, the case containing the instrument is packaged, delivered and prepared in packaging means 6. These packaging means, which are disposable and made out of flexible plastic, comprise two parts 61, 62 provided with thin walls which the practitioner separates when he wishes to use the instrument protected by the case contained inside (FIG. 6). After a partial opening of the package, the instrument can be brought closer to the instrument-holder and then installed on this holder without any direct contact being required between the practitioner and the instrument or even between the practitioner and the case.

6.4. Means for Receiving and Retaining the Instrument

Figure 8:
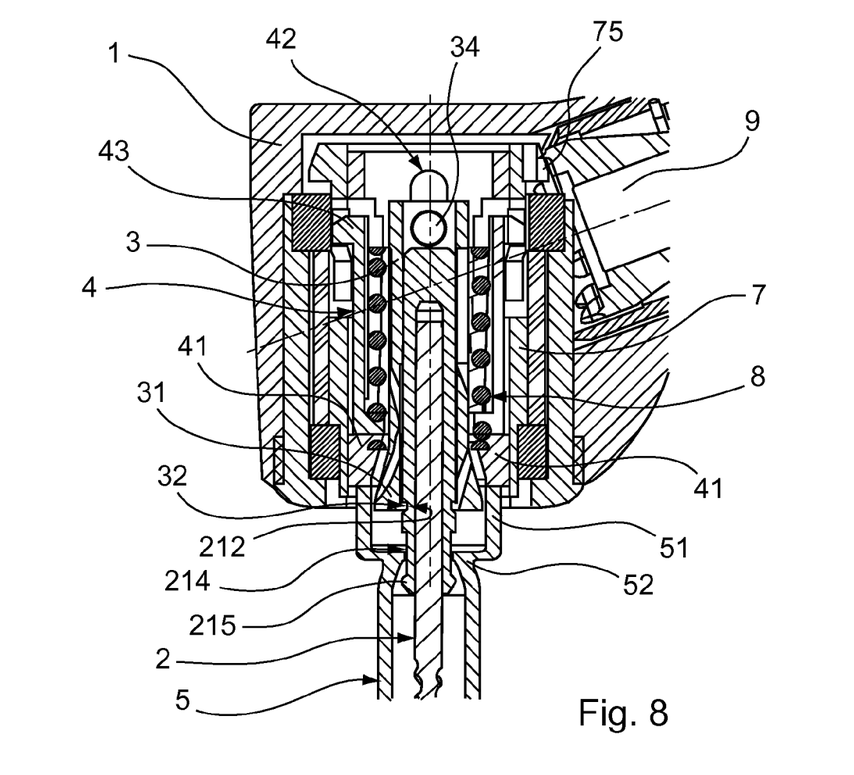
FIG. 8 is an illustration, in section, of an apparatus for dentists according to one embodiment of the invention with the receptacle in a retaining position and the locking/unlocking unit in an unlocking position.
Figure 10:
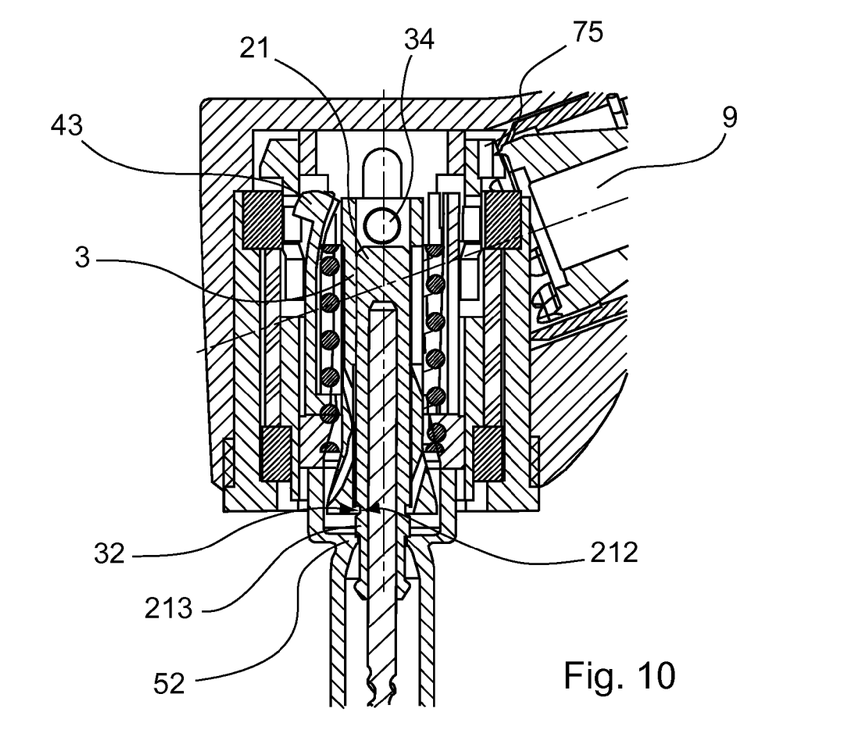
FIG. 10 is an illustration, in section, of the apparatus for dentists of FIG. 8 with the receptacle in a retaining position and the locking/unlocking unit in transition between its unlocking and locking positions.
Figure 12:
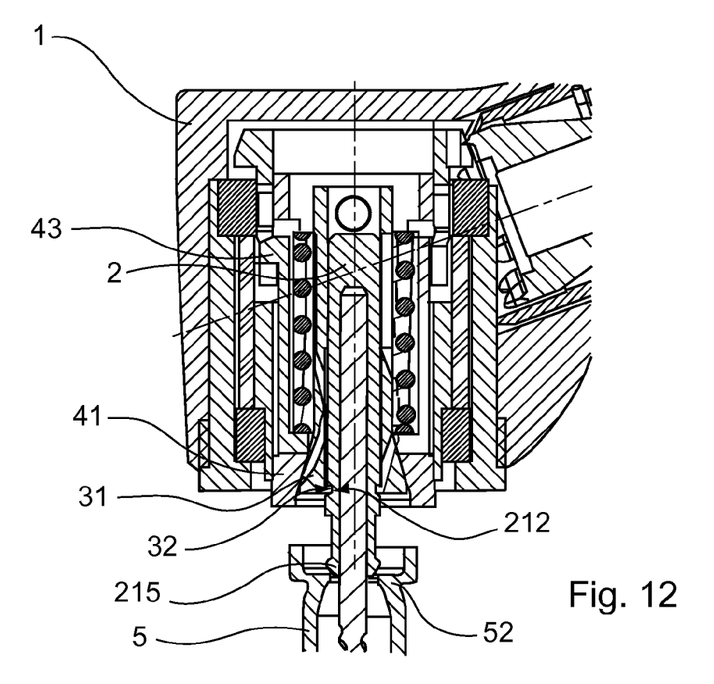
FIG. 12 is an illustration, in a sectional view, of the apparatus for dentists of FIGS. 8 and 10 with the receptacle in a position of retaining and the locking/unlocking unit in a locking position.

The instrument 2 is received and retained in the instrument-holder 1 by means for receiving and retaining constituted by a receptacle 3 and a locking/unlocking unit 4 as shown in FIGS. 8, 10 and 12.

Figure 14A:
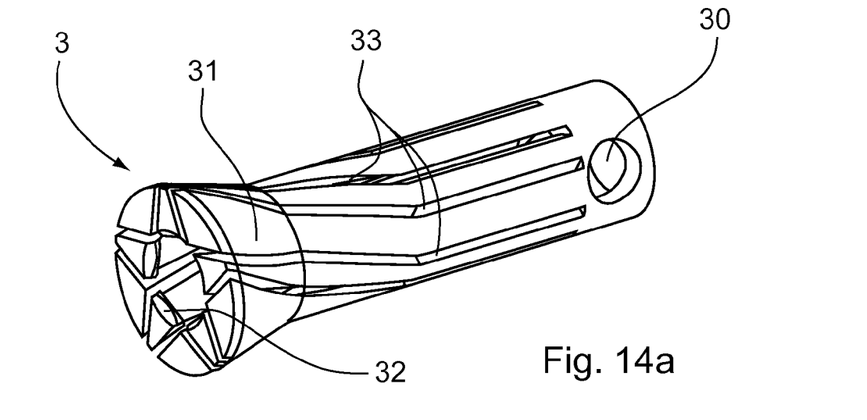
FIGS. 14a and 14b are illustrations, in a perspective view, of a receptacle made according to two preferred embodiments of the invention.
Figure 14B:
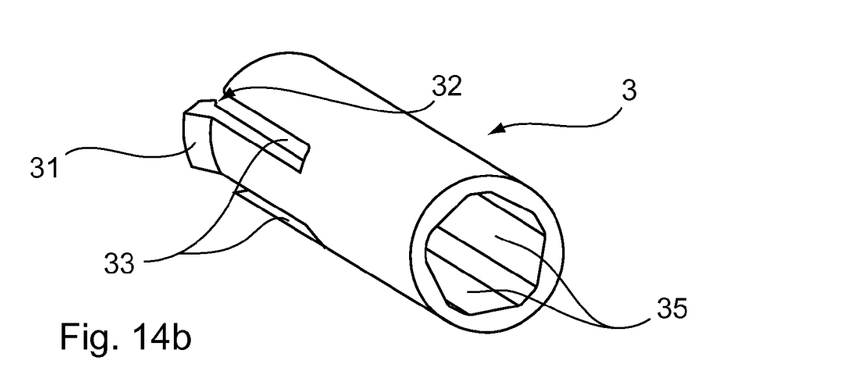

The receptacle 3, illustrated in isolation in FIGS. 14a and 14b, in two preferred embodiments, has a tube shape.

At one of its ends, it has a diametral bore 30 (not visible in FIG. 14b) intended for receiving an attachment means such as a pin 34. At the opposite end, it has a flared-out base 31 that follows a conical shape provided with a projecting internal lip 32 that extends radially towards the interior of the receptacle.

The receptacle furthermore comprises longitudinal recesses 33 such that they can get deformed elastically in a radial direction, chiefly at its base 31. This mobility enables the internal lip (or toe) 32 to enter the groove 212 of an instrument during assembly or to be removed from this groove.

Thus, the receptacle 3 has a base 31 provided with at least one radially mobile toe 32 and the instrument 2 has at least one recess 212 designed to receive the toe in its retaining position.

The deformation of the receptacle 3 enables it to oscillate between a configuration in which it is sufficiently open to enable the introduction or withdrawal of an instrument (the open position) and a configuration in which it can retain an instrument, especially by its internal lip (or toe) 32 (the retaining position). Preferably, this receptacle has an elasticity tending to bring it into its retaining position or to a position close to its retaining position.

Besides, the hollow internal part of the receptacle 3 has shapes 35 (flat surfaces, etc) complementary to the flat surfaces 31 of the shank 21 of the instrument. Thus, the instrument 2 introduced into the receptacle occupies a position that is locked in rotation.

The locking/unlocking unit 4 has a general tubular shape and dimensions that enable it to contain the receptacle 3.

The base 41 of the locking/unlocking unit 4 has a conical internal shape which cooperates with the conical base 31 of the receptacle 3 (FIG. 12).

When the base 41 envelops the base 31 this base 31 is radially contracted, thus maintaining the receptacle 3 in its retaining position in which it retains an instrument 2 preliminarily introduced into the receptacle 3. Conversely, the moving away of the conical surface from the base 31 relative to the conical surface of the base 31 radially releases the receptacle, and this enables it to pass into an open position where an instrument can be inserted or withdrawn.

Figure 7:
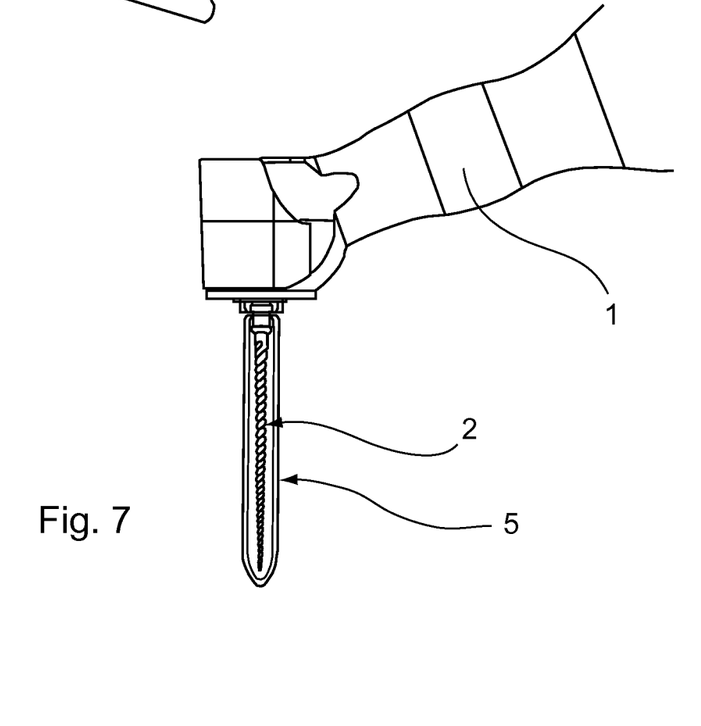
FIG. 7 is an illustration, in a side view, of the instrument-holder (seen partially), the instrument and the case of FIG. 6, in a mounting position.

During the mounting and dismounting of the instrument 2, the case 5 is brought against the instrument-holder 1 (FIG. 7). The external surface of the ring 51 of the case is then in contact with the external surface of the base 41 of the locking/unlocking unit (FIG. 8).

It must be noted that the instrument 2 has a certain degree of freedom in rotation in the case 5, especially in the case illustrated by FIG. 5a ('ring-shaped' internal lip 52). The instrument can then easily rotate about its axis inside the case when it is inserted into the receptacle 3 in order to reach a position in which its flat surfaces 211 get engaged against the complementary shapes 35 present within the receptacle. However, the practitioner always keeps the possibility of making the case/instrument set rotate between his fingers in order to facilitate the introduction of the instrument into the receptacle.

Thus, the apparatus for dentists as illustrated comprises:
  at least one instrument-holder 1 comprising means for receiving and retaining a dental surgical instrument 2, and
  at least one dental surgical instrument 2 intended for being mounted on the instrument-holder 1.

More specifically, the means for receiving and retaining comprise:
  a receptacle 3 for receiving the instrument, mobile between an open position permitting the introduction of the instrument into the instrument-holder and the withdrawal of the instrument from the instrument-holder, and a retaining position;
  a unit 4 for locking/unlocking the receptacle in the retaining position.

Moreover, the apparatus for dentists comprises a case 5 in which the instrument 2 is housed, this case having an element for cooperating, in this case a ring 51, designed to cooperate with the locking/unlocking unit 4 to cause it to pass from the locking position in which it locks the receptacle 3 in its retaining position to the unlocking position in which it does not lock this receptacle and enables it to pass into its open position, or vice versa.

To this end, the instrument-holder 1 has a body 7 in which the locking/unlocking unit 4 is mounted slidingly as well as a return spring 8 between the body 7 and the locking/unlocking unit 4, the spring tending to push the locking/unlocking unit towards the locking position where it locks the receptacle in the retaining position.

As illustrated in FIG. 1, the locking/unlocking unit 4 has a cylindrical part 44 extending out of the body of the instrument-holder 1.

Moreover, the pin 34 enables the receptacle 3 to be fixedly attached to the body 7 in passing through the locking/unlocking unit at an oblong aperture 42 (FIG. 8).

In addition, the body 7, the receptacle 3 and the locking/unlocking unit 4 extend along the same longitudinal direction. In this way, the locking/unlocking unit 4 is also mounted slidingly relative to the receptacle 3.

The spring 8 naturally pushes the locking/unlocking unit 4 towards its locking position.

In the contrary sense, a pressure of the case 5 on the locking/unlocking unit comprises the spring and tends to bring the locking/unlocking unit 4 to its unlocking position.

6.5. Mounting and Dismounting of the Instrument

During the mounting and dismounting of the instrument 2 relative to the instrument-holder 1, an apparatus for dentists according to the invention then has several configurations with positions which follow one another in a predefined order, according to the following description.

This description is illustrated by FIGS. 8 to 13 in which the case represented is, for example, semi-rigid and as described here above with reference to FIG. 5a.

Figure 13:
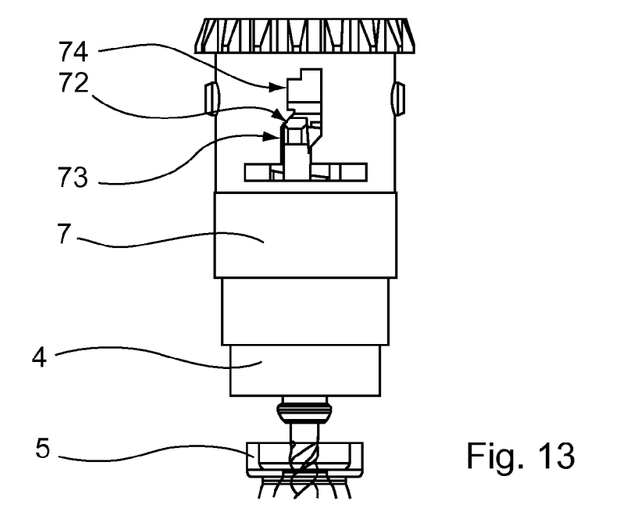
FIG. 13 is an illustration, in a front view, of the body of the instrument-holder of the apparatus of FIG. 12 in a position corresponding to that of FIG. 12.

First of all, the locking position for locking the means for receiving and retaining the instrument 2 in the instrument-holder 1, as it exists when the apparatus for dentists is in operation, is illustrated in FIGS. 12 and 13.

The base 31 of the receptacle 3, in its retaining position, firmly retains the instrument 2, especially by gripping the inner lip 32 in the groove 212. The locking/unlocking unit 4, which is in its locking position, maintains the receptacle 3 in the retaining position.

This locking position is stable, i.e. the instrument 2 remains held in the instrument-holder without any action by the practitioner so long as no external force (such as a force exerted on the locking/unlocking unit 4 by the case 5) is applied.

The case 5 can then be withdrawn from or inserted relative to the instrument 2 in position, by a manual force in which the internal lip 52 is made to cross the beveled ring 215 (since the diameter of the beveled ring is greater than that of the internal lip, this lip by its flexibility can get deformed when crossing the beveled ring).

FIG. 13 is a partial view of the case, detached from the instrument.

Figure 9:
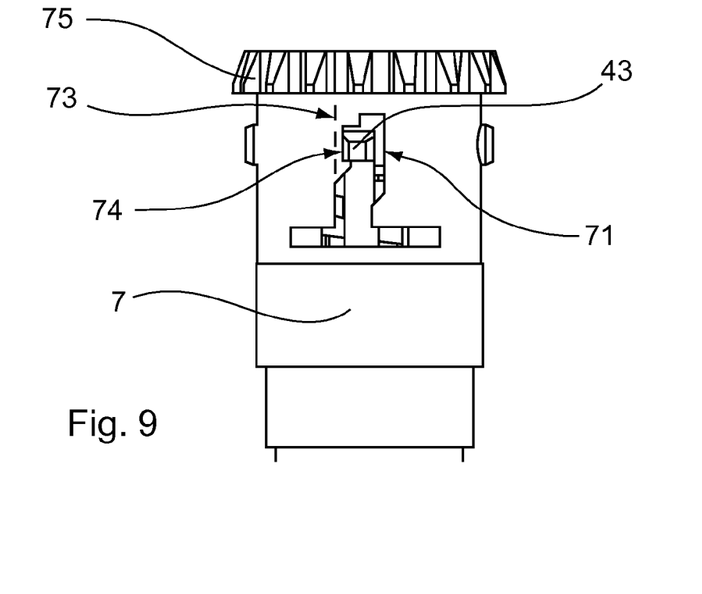
FIG. 9 is an illustration, in a front view, of the instrument-holder body of the apparatus of FIG. 8 in a position corresponding to that of FIG. 8.

FIGS. 8 and 9 illustrate a position of unlocking of the receiving and retaining means, achieved by pushing the case 5 on the locking/unlocking unit 4 from the previous locking position, in order to withdraw an instrument 2 from the instrument-holder 1.

Referring to FIG. 8, the locking/unlocking unit 4 is in an unlocked position in which it does not act on the receptacle. The receptacle 3 however remains in its retaining position in which the inner lip 32 is still present in the groove 212 but in an unlocked way so that it still exerts a slight retaining force, preventing the instrument from dropping gravitationally and enabling the practitioner to extract it by hand, using the case.

The instrument mounted in the instrument-holder is removed through the particular cooperation between the groove 214 and the inner lip 52 of the case, enabling the receptacle 3 to be made to pass into its open position: in one sense, first of all, the practitioner forces the internal lip to cross the beveled ring 215 (or to sheath the smooth cylindrical end 2140 in the case of a flexible case), to fit the case onto the instrument; then, in the contrary sense, a pulling force on the case forces the internal lip 32 of the receptacle to move away and release the instrument, the internal lip 52 then abutting the beveled ring 215 (or in the case of a flexible case, an appropriate pressure by the practitioner's fingers on this case is sufficient to grasp the instrument and hold it throughout the withdrawing motion).

To introduce a new instrument into the instrument-holder, the receptacle must also be in this open position.

It can be noted that should the locking/unlocking unit 4 be put in the locking position while the receptacle contains no instrument, simple pressure by means of an empty case on the locking/unlocking unit 4 is enough to place it in this unlocking position.

An instrument 2 can then again be introduced into the receptacle. Now, the external diameter of the shank 21 of the instrument is greater than that of the internal lip 32 'at rest'. The internal lip then therefore moves away gradually, up to the open position of the receptacle to allow the instrument, through the rounded or chamfered shape of its shank 21, to penetrate the instrument when the practitioner exerts pressure by means of the case containing the instrument. It can be noted that the internal lip 32 then puts up a resistance against the instrument which can lead the internal lip 52 of the case to slide up to the stop ring 213.

In this position, the instrument slides in the receptacle until the case 5 comes into contact with the locking/unlocking unit 4. The internal lip 32 is then out of the groove 212 of the instrument.

This unlocking position of the locking/unlocking unit is stable because of the presence, on the locking/unlocking unit, of a catch 43 which is elastically deformable, cooperating with a housing 71 made by a cut in the body 7. The catch 43 is held in position by the combined action of the spring 8 and a tangential stress which presses it against the plane 74 of the housing 71.

The apparatus therefore remains in this position, if the practitioner relaxes the pressure put on the case in order to reach it.

To reach this stable unlocking position of the locking/unlocking unit in the body, from the locking position, the catch changes its position but does not leave the housing 71 (from the position of FIG. 13 to the position of FIG. 9) in going along an inclined plane 72 by means of its lateral mobility. In passing, the catch gets wedged against the plane 74 whereas it is initially wedged against a plane 73 parallel to the plane 74.

Figure 11:
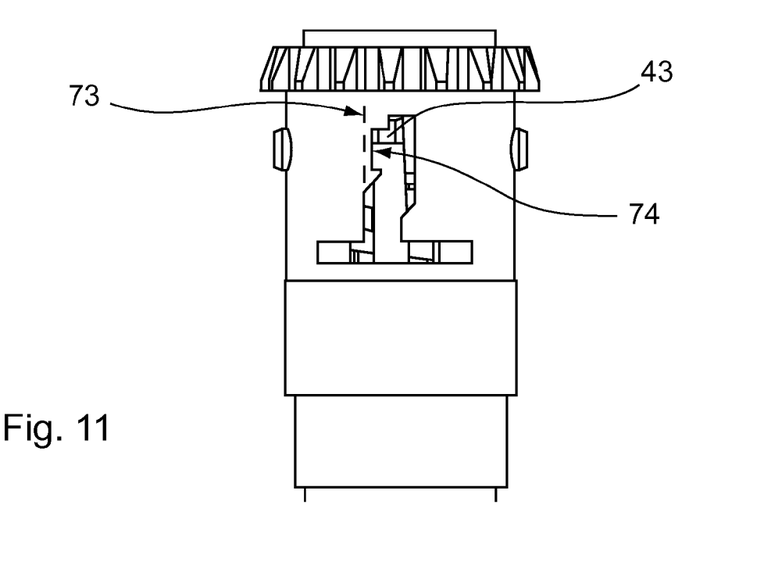
FIG. 11 is an illustration, in a front view, of the body of the instrument-holder of the apparatus of FIG. 10 in a position corresponding to that of FIG. 10.

To then return to the locking position which makes it possible to maintain the instrument 2 that the dentist has just inserted into the instrument-holder 1, he must first of all make the case 5 exert renewed pressure on the locking/unlocking unit 4 until this unit reaches the position illustrated in FIGS. 10 and 11.

In this position, the shank 21 of the instrument 2 abuts the pin 34 at the bottom of the receptacle 3, the internal lip 52 of the case 5 is in contact with the stop ring 213 while the internal lip 32 of the receptacle penetrates the groove 212 of the instrument.

The locking/unlocking unit 4 is then in an unlocking position but one that is no longer stable. Indeed, during the thrust leading to this position, the catch 43 remains first of all in the housing 71 and then the chamfered ridges and the radial mobility of the catch enable it to come out of the housing 71 according to FIG. 11. The position reached is therefore not stable.

Now, the catch 43 comes out of the housing 71 in an inclined path, relative to the sliding axis of the locking/unlocking unit. It therefore tends to shift laterally within the body, out of the housing, towards the plane 73. The gradual release of the case, combined with the thrust of the spring, then enables the locking/unlocking unit to slide up to its locking position without the catch being able to stop it in the unlocking position illustrated in FIGS. 8 and 9. The catch then re-enters the housing, against the plane 73. Thus, the locking/unlocking unit 4 presents a catch 43 that is radially mobile and laterally intended to cooperate with the housing 71 made in the body 7. This catch advantageously gives the locking/unlocking unit a bistable state, i.e. this locking/unlocking unit can be stable both in its locking position and in its unlocking position.

During the movement towards its locking position, the locking/unlocking unit 4 compresses the conical base 31 of the receptacle 3 and the internal lip 32 remains positioned in the groove 212 of the instrument 2. At the end of this movement, the instrument has therefore kept its axial positioning relative to the receptacle and is firmly retained by this unit.

The elasticity of the receptacle and the presence of the longitudinal recesses also improves the gripping of the instrument by increasing the surfaces in contact with the shank of the instrument so that no clearance remains between the instrument and the receptacle.

A homogenous distribution of the gripping forces is furthermore obtained throughout the surface of the shank of the instrument. Thus, even when the shank of the instrument is made out of plastic, the risk that it might break is considerably reduced and it combines the advantages of plastic materials (easy color identification, low cost, etc) and of metallic materials (solidity, efficient transmission of the rotational torque, etc).

In short, the receiving and retaining means of the equipment pass from:
- the locking position illustrated by FIG. 12 to the unlocking position illustrated by FIG. 8, when the practitioner dismounts an instrument present in the instrument-holder;
- the unlocking position illustrated by FIG. 8 to the locking position illustrated by FIG. 12, in passing through the unstable intermediate position illustrated by FIG. 10 when the practitioner mounts an instrument in the instrument-holder.

It can be noted that the body 7, as illustrated by FIGS. 8, 10 and 12, is driven rotationally through the interlocking of its teeth 75 with those of the drive means 9 presented in the sleeve of the instrument-holder 1. The body 7 can thus itself drive the instrument 2 in rotation.

It can be noted that a similar operation can be obtained by mounting a spring such as the spring 8 between the locking/unlocking unit 4 and not the body 7 but the receptacle 3. This variant however can be less advantageous because the spring can be in an awkward position during the changes of receptacle that are likely to be made.

6.6 Temporary Storage Means

Figure 15:
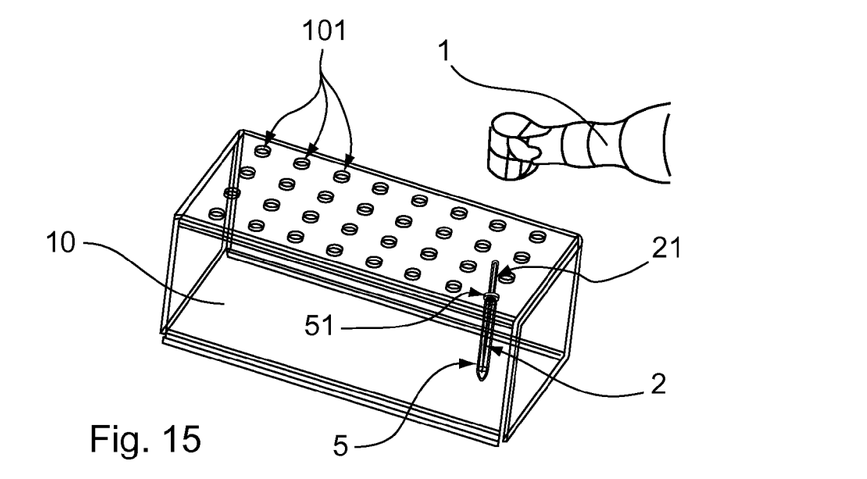
FIG. 15 is an illustration, in a perspective view, of an instrument-holder, an instrument and a case according to one embodiment of the invention as well as a means of temporary storage in which lies the case containing the instrument.

According to one preferred embodiment illustrated in FIG. 15, the apparatus for dentists according to the invention is used with a temporary storage means 10 which can receive cases 5 designed to receive an instrument 2. This means is provided with recesses 101 (32 in this case) which are made to receive an equivalent number of cases in such a way that the part 51 of each case and the shank 21 of the instrument possibly supported by the case project to the exterior of the means. Thus the practitioner can grasp each case by its part 51 or present the instrument-holder 1 directly to the shank 21 of the instrument.

These means are particularly useful for supporting several instruments likely to be used one or more times by the dentist during a same operation in an ordered way and to present these instruments ergonomically. The instrument-changing times are then minimized. Since the contact with the case is reduced or even eliminated, the aseptic conditions of use of the apparatus are also improved.

Other embodiments, based on the principle of an apparatus for dentists such as the one that has just been described can of course be envisaged without departing from the framework of the invention.

More particularly, systems other than an elastic catch can be envisaged to obtain stable locking and unlocking positions for the receiving and retaining means (rotary barrel system especially).

An exemplary embodiment of the invention proposes a mechanized surgical instrument comprising an instrument and an instrument-holder to improve the conditions of use as regards asepsis.

An exemplary embodiment of the invention provides a mechanized surgical apparatus of this kind comprising an instrument and an instrument-holder improving its conditions of use at the ergonomical level.

The invention claimed is:

1. A mechanized surgical apparatus comprising:
   at least one instrument-holder, which receives and retains a surgical instrument for mechanized use, and
   at least one surgical instrument for mechanized use, mountable on said instrument-holder, said instrument comprising a shank, which cooperates with the instrument-holder, and an active blade, wherein said instrument holder comprises:
   an unlocking position, which enables introduction of said shank of the instrument into the instrument-holder or withdrawal of said shank from the instrument-holder; and
   a locking position, which prevents the withdrawal of said shank from the instrument-holder;
   a receptacle configured to receive and maintain said shank of the instrument, said receptacle being mobile between an open position, permitting introduction of said shank into said receptacle or withdrawal of said shank from said receptacle, and a retaining position in which the receptacle retains said shank in said receptacle; and
   a locking/unlocking unit, mobile between said locking position in which the unit holds said receptacle in said retaining position, and said unlocking position in which the unit does not hold said receptacle in said retaining position;
   a case configured to detachably house said active blade of said instrument, said case having a cooperating element shaped to cooperate with said locking/unlocking unit to cause the locking/unlocking unit to pass from said unlocking position to said locking position, or vice versa, and wherein the case is detachable from and attachable to the active blade of said instrument when the instrument is retained by the instrument holder.

2. The mechanized surgical apparatus according to claim 1, wherein said unlocking and locking positions are stable positions.

3. The mechanized surgical apparatus according to claim 1, wherein said instrument-holder comprises a body in which the locking/unlocking unit is mounted slidingly, said locking/unlocking unit having at least one mobile catch that cooperates with at least one housing made in said body.

4. The mechanized surgical apparatus according to claim 3, wherein said catch is radially and laterally mobile.

5. The mechanized surgical apparatus according to claim 3, wherein said catch is elastically deformable.

6. The mechanized surgical apparatus according to claim 1, wherein said locking/unlocking unit is mounted slidingly relative to said receptacle.

7. The mechanized surgical apparatus according to claim 1, wherein said receptacle has a base provided with at least one radially mobile toe, said shank of the instrument having at least one recess configured to receive said toe in said retaining position.

8. The mechanized surgical apparatus according to claim 1, wherein said instrument-holder comprises a return spring between said body and said locking/unlocking unit, said spring tending to push said locking/unlocking unit towards said locking position.

9. The mechanized surgical apparatus according to claim 1, wherein said locking/unlocking unit has a part extending out of the body of the instrument-holder.

10. The mechanized surgical apparatus according to claim 9, wherein said part is cylindrical.

11. The mechanized surgical apparatus according to claim 1, wherein said cooperating element of the case is a ring.

12. An instrument-holder comprising:
   an unlocking position, which enables introduction of a shank of a surgical instrument for mechanized use into the instrument-holder or withdrawal of said shank from the instrument-holder;
   a locking position, which prevents the withdrawal of said shank from the instrument-holder;
   a receptacle configured to receive and maintain said shank of the instrument, said receptacle being mobile between an open position, permitting introduction of said shank into said receptacle or withdrawal of said shank from said receptacle, and a retaining position in which the receptacle retains said shank in said receptacle; and
   a locking/unlocking unit, mobile between said locking position in which the unit holds said receptacle in said retaining position, and said unlocking position in which the unit does not hold said receptacle in said retaining position wherein the locking/unlocking unit is shaped to cooperate with a cooperating element of a case that detachably houses an active element of linked to said surgical instrument to cause said locking/unlocking unit to pass from the unlocking position to the locking position, or vice versa.

* * * * *